(12) United States Patent
Han et al.

(10) Patent No.: US 6,572,901 B2
(45) Date of Patent: Jun. 3, 2003

(54) PROCESS FOR MAKING A CHEESE PRODUCT USING TRANSGLUTAMINASE

(75) Inventors: Xiao-Qing Han, Naperville, IL (US); Jochen Klaus Pfeifer, Penzberg (DE); Richard H. Lincourt, Mundelein, IL (US); Joseph Michael Schuerman, Prospect Heights, IL (US)

(73) Assignee: Kraft Foods Holdings, Inc., Northfield, IL (US)

( * ) Notice: Subject to any disclaimer, the term of this patent is extended or adjusted under 35 U.S.C. 154(b) by 0 days.

(21) Appl. No.: 09/847,694

(22) Filed: May 2, 2001

(65) Prior Publication Data

US 2003/0054069 A1 Mar. 20, 2003

(51) Int. Cl.$^7$ .................................................. A23C 9/12
(52) U.S. Cl. .............................. 426/36; 426/34; 426/38; 426/39; 426/40; 426/42; 426/43; 426/52; 426/582
(58) Field of Search ............................ 426/34, 36, 38, 426/39, 40, 42, 43, 52, 580, 582

(56) References Cited

U.S. PATENT DOCUMENTS

| | | | |
|---|---|---|---|
| 5,156,956 A | | 10/1992 | Motoki et al. |
| 5,681,598 A | | 10/1997 | Kuraishi et al. |
| 5,731,183 A | | 3/1998 | Kobayashi et al. |
| 6,093,424 A | | 7/2000 | Han et al. |
| 6,242,036 B1 | * | 6/2001 | Han et al. ............... 426/582 |
| 6,258,390 B1 | * | 7/2001 | Budtz ..................... 426/36 |
| 6,270,814 B1 | * | 8/2001 | Han et al. ................. 426/36 |
| 6,406,736 B1 | * | 6/2002 | Han ........................ 426/582 |
| 6,416,797 B1 | * | 7/2002 | Han et al. ................. 426/36 |
| 6,419,975 B1 | * | 7/2002 | Han et al. ............... 426/582 |

FOREIGN PATENT DOCUMENTS

| | | |
|---|---|---|
| EP | 0711 501 A1 | 5/1995 |
| EP | 1 048 218 A2 | 11/2000 |
| JP | 59-59151 | 4/1984 |
| JP | 2-276541 | 11/1990 |
| WO | WO 97/01961 | 1/1997 |

OTHER PUBLICATIONS

Folk, J.E. and P.W. Cole. "Structural Requirements of Specific Substrates for Guinea Pig Liver Transglutaminase." *The Journal of Biological Chemistry* 240.7 (Jul. 7, 1965) : 2951–2960.

Laemmli, U.K. "Cleavage of Structural Proteins during the Head of bacteriophage T4." *Nature* Aug. 15, 1970:680–685.

Lowry, Oliver, Nira J. Rosebrough, A. Lewis Farr, and Rose J. Randall. "Protein Measurement with the Folin Phenol Reagent." *Journal of Biological Chemistry* 193 (1951); 265.

* cited by examiner

Primary Examiner—Leslie Wong
(74) Attorney, Agent, or Firm—Fitch, Even, Tabin & Flannery

(57) ABSTRACT

The current invention provides an improved process for making a cheese product using transglutaminase. The method comprises the steps of providing a dairy liquid, crosslinking and curding the dairy liquid by adding an acidifying agent and a transglutaminase to the dairy liquid under conditions sufficient to crosslink at least a portion of proteins in the dairy liquid to provide both a curd comprising a crosslinked dairy liquid and a liquid whey, cutting and cooking the curd, separating the curd from the liquid whey, and collecting the curd. Many specific embodiments are provided. Additionally, the current invention provides a product made by the process. The cheese products, especially soft cheeses such cream cheese and cottage cheese, exhibit less syneresis than similar cheeses prepared by conventional methods.

14 Claims, 6 Drawing Sheets

PROCESS FOR MAKING A CHEESE PRODUCT USING TRANSGLUTAMINASE

FIELD OF THE INVENTION

The invention relates to the production of cheese, especially cream cheese and cottage cheese. More specifically, the invention relates to methods for increasing dairy protein incorporation into curd during cheese production using transglutaminase. This invention also relates to methods for reducing syneresis in cheese products, especially cream cheese and cottage cheese, using transglutaminase.

BACKGROUND

Cheese compositions are generally prepared from dairy liquids by processes that include treating the liquid with a coagulating or clotting agent. The coagulating agent may be a curding enzyme, an acid, or a suitable bacterial culture. The coagulum or curd that results generally incorporates transformed casein, fats including natural butter fat, and flavorings (especially those arising when bacterial cultures are used). The curd is usually separated from the whey. The resulting liquid whey generally contains soluble proteins not affected by the coagulation; such proteins are, of course, not incorporated into the coagulum. The inability of whey proteins to be retained in the coagulum is an important factor contributing to a lack of efficiency in production of cheese curds, and to a reduction in overall yield relating to the incorporation of protein solids present in the starting dairy liquids into resulting cheese curds. Therefore, there remains a need for effective methods of improving the efficiency of protein incorporation into curd during cheese production.

Soft cheeses such as cream cheese and cottage cheese products usually suffer water separation during storage due to the process of syneresis. The resulting acid whey (i.e., separated water phase), although it contains substantial amounts of dairy proteins, cannot be efficiently utilized. Moreover, consumers generally find such water separation objectionable. Therefore, there remains a need for improved methods for producing soft cheeses wherein syneresis is reduced.

Transglutaminases are enzymes which catalyze the crosslinking of proteins. These enzymes have a broad occurrence in nature and may be obtained, for example, from microorganisms such as those belonging to the genus Streptoverticillium or from *Bacillus subtilis*, from various Actinomycetes and Myxomycetes, from fish and other marine sources, from plant sources, and from animal sources (especially mammals). Food processing methods employing transglutaminases have been disclosed in recent years. For example, Japanese Patent 59059151 discloses treating an emulsion containing proteins, oils or fats, and water with transglutaminase to produce a gelatinous, crosslinked gel. Japanese Patent 02276541 discloses a heat-resistant food protein having a fibrous texture. The fibrous texture is developed by treatment of a protein hydrogel with a transglutaminase in the presence of calcium ions to induce crosslinking of the surface of a fiber bundle.

U.S. Pat. No. 5,156,956 discloses a transglutaminase purified from strains of the genus Streptoverticillium, and the use of this enzyme to produce gel type foods. This transglutaminase catalyzes formation of protein gelation products from protein solutions to produce conventional gel foodstuffs such as yoghurt, jelly, cheese, gel cosmetics, and the like.

U.S. Pat. No. 5,731,183 discloses a transglutaminase purified from strains of *Bacillus subtilis*, having particular physical and enzymatic characteristics, and a method for producing protein, peptide, or non-protein amino acid polymers that are crosslinked via their glutamine and lysine residues to form intermolecular or intramolecular conjugates. The crosslinked protein polymers produced using transglutaminase are reported to be useful in a variety of food substances.

Methods have been proposed for increasing the recovery of whey protein into cheese products using transglutaminase. For example, U.S. Pat. No. 6,093,424 relates to treatment of a dairy liquid such as milk with transglutaminase and a non-rennet protease to generate cheese curd for hard, soft, or semi-soft cheeses.

U.S. Pat. No. 5,681,598 and its European counterpart EP 0 711 504 A1 disclose a process for producing cheese using transglutaminase added at the same time as both a clotting enzyme and a lactic-acid producing culture, and the milk is then incubated.

Patent publication WO 97/01961 discloses a method for producing cheese using transglutaminase. Transglutaminase is added to milk, followed by a short incubation period, after which a clotting enzyme or curding agent is added to the milk to produce curd.

The current invention provides processes for producing cheeses that improve the efficiency of dairy protein incorporation into cheese curd during production. Additionally, the cheeses produced using the process have improved qualities, including decreased syneresis.

SUMMARY OF THE INVENTION

The current invention provides processes for cheese manufacturing that significantly increase the yield of cheese produced by using the enzyme transglutaminase and an acidifying step to crosslink dairy proteins during cheese manufacturing. The cheese products are less fragile and have reduced syneresis. Additionally, the cheese products have greater viscosity and firm texture.

In one aspect, the current invention provides a process for making a cheese product comprising:
(i) providing a dairy liquid comprising dairy proteins;
(ii) crosslinking and curding the dairy liquid by adding an acidifying agent and adding a transglutaminase to the dairy liquid for a crosslinking and curding time, and under crosslinking and curding conditions, sufficient to crosslink at least a portion of the dairy proteins and to form a curd and a liquid whey;
(iii) disrupting and heating the curd;
(iv) separating the curd from the liquid whey; and
(v) collecting the curd.

Typically, a coagulating enzyme is not added during step (ii). In certain embodiments, a coagulating enzyme is not added during any step of the process. The dairy liquid may be pasteurized.

In certain embodiments, transglutaminase is used in step (ii) at concentrations of less than 10 units per gram dairy liquid, preferably less than 5 units per gram, more preferably less than 1 unit per gram. In certain embodiments, transglutaminase is used at a concentration of about 0.4 to about 0.8 units per gram dairy liquid.

In one embodiment, the addition of the acidifying agent during step (ii) is performed before the addition of transglutaminase. In a further embodiment, the process further comprises heating the crosslinked dairy liquid at a temperature and for a time sufficient to inactivate the transglutaminase after step (ii) and before step (iii).

In certain embodiments, the acidifying agent is a culture containing a lactic acid-producing microbe. In one embodiment using a lactic acid-producing microbe, the resulting pH of the dairy liquid is about 4.2 to about 5.2, preferably about 4.4 to about 4.8, and most preferably about 4.5 to about 4.7.

In certain embodiments, the acidifying agent is a food grade acid. In one embodiment, the food grade acid is selected from the group consisting of citric acid, lactic acid, glucono delta lactone, phosphoric acid, acetic acid or vinegar, and the like.

In certain embodiments, the dairy liquid comprises dairy ingredients selected from milk, reconstituted dry milk, concentrated milk, milk protein concentrate, whey, reconstituted whey, whey protein concentrate, and cream.

In certain embodiments, the dairy liquid comprises cream and a dairy ingredient selected from the group consisting of milk, reconstituted dry milk, concentrated milk, milk protein concentrate, whey, reconstituted whey, and whey protein concentrate. For these embodiments, the cheese is typically cream cheese. In one embodiment where the cheese is cream cheese, the cooking in step (iv) is performed by heating the curd and whey to about 80° C. for about 30 minutes.

In certain embodiments, the dairy liquid is skim milk, concentrated skim milk, reconstituted nonfat dry milk, whey protein, or milk protein concentrate. Typically, where the dairy liquid is skim milk, the resulting cheese is cottage cheese. In one embodiment where the dairy liquid is skim milk, the cooking in step (iv) is performed by increasing the temperature of the curd and whey from about 30 to about 60° C. over a period of about 15 to about 150 minutes, and more preferably over a period of about 60 minutes. Typically, where the resulting cheese is cottage cheese, the crosslinking and curding time is from about 1 hour to about 14 hours and the crosslinking and curding conditions include a temperature of about 15 to about 55° C., preferably from about 3 hours to about 6 hours at a temperature of about 30 to about 34° C., more preferably at about 32° C.

Typically, where the resulting cheese is cream cheese, the crosslinking and curding time is from about 1 hour to about 24 hours and the crosslinking and curding conditions include temperatures of about 18 to about 50° C., preferably from about 15 hours to about 19 hours at a temperature of about 22 to about 28° C. In one embodiment, the crosslinking and curding is carried out for about 17 hours at a temperature of about 25° C.

In significant embodiments of the process of the present invention, the transglutaminase is isolated from a bacterial source, a fungus, a mold, a fish, or a mammal. In one preferred embodiment, the transglutaminase is isolated from a bacterial source, preferably from the genus Streptoverticillium. Mixtures of transglutaminase from different sources can be used.

The processes of the current invention for making cream cheese products may include an additional homogenization step after the curd is collected. The homogenization may be carried out at pressures of up to about 10000 psi, preferably up to about 3500 psi, and most preferably up to about 5000 psi.

In another aspect, the current invention is a cheese product produced by a process as described above, including any of the embodiments described above.

DESCRIPTION OF THE PREFERRED EMBODIMENTS

Figure 1:
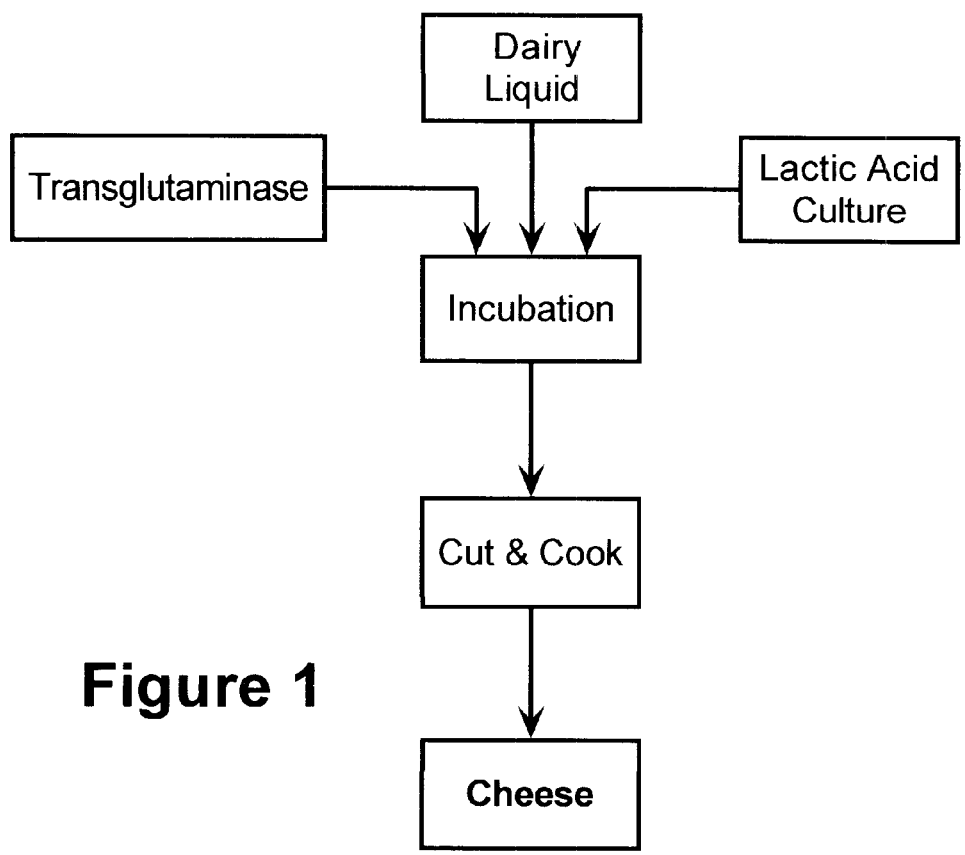
FIG. 1 is a flow diagram illustrating the general process of the current invention.

The general process of this invention is illustrated in FIG. 1. The starting material is a dairy liquid which may or may not be pasteurized. As used herein, "dairy liquid" refers to milk, milk products obtained by fractionating raw milk to provide a liquid fraction, or a solid milk fraction that is reconstituted to a liquid. For example, the milk may be treated to remove some or all of the butterfat, providing low fat milk or skim milk, respectively. Furthermore, whole milk, low fat milk, or skim milk may be concentrated by methods such as evaporation and/or ultrafiltration (with or without diafiltration) and the like. Evaporation provides dairy liquids containing a higher concentration of all the nonvolatile components, whereas ultrafiltration provides dairy liquids with a higher concentration of the components that do not permeate the ultrafiltration membrane. In any case, the dairy proteins including casein and whey protein are included among the retained solids, such that their concentrations in the resulting liquids are increased. Furthermore, any of the above dairy liquids may be evaporated to dryness, providing milk solids originating from whole milk, low fat milk, or skim milk, and including casein, whey proteins, and lactose. Any of these solids may be reconstituted by the addition of water or a suitable aqueous composition including milk or a milk fraction. Reconstitution of dry milk thus provides dairy liquids that in general may have a broad range of final concentrations of the component proteins, lactose, butterfat, and other components. All the above liquids are included in the designation of "dairy liquids" as used herein.

The dairy liquids employed in the present invention may originate from any lactating livestock animal whose milk is useful as a source of human food. Such livestock animals include, by way of nonlimiting example, cows, buffalo, other ruminants, goats, sheep, and the like. Generally, however, cows' milk is the preferred dairy liquid used in the practice of the invention.

As used herein, "casein" relates to any, or all, of the phosphoproteins in milk, and to mixtures of any of them. An important characteristic of casein is that it forms micelles in naturally occurring milk and in the dairy liquids employed in the present invention. Many casein components have been identified, including, but not limited to, α-casein (including $\alpha_{s1}$ casein and $\alpha_{s2}$ casein), β-casein, κ-casein, and their genetic variants.

As used herein, "whey protein" relates to the proteins contained in the dairy liquid (i.e., whey) obtained as a supernatant of the curds when milk or a dairy liquid containing milk components are curded to produce a cheese-making curd as a semisolid. Whey protein is generally understood to include the globular proteins β-lactoglobulin and α-lactalbumin. It also includes significantly lower concentrations of immunoglobulin, other globulins, and trace amounts of caseins depending on the process of curding and/or whey separation.

Figure 2:
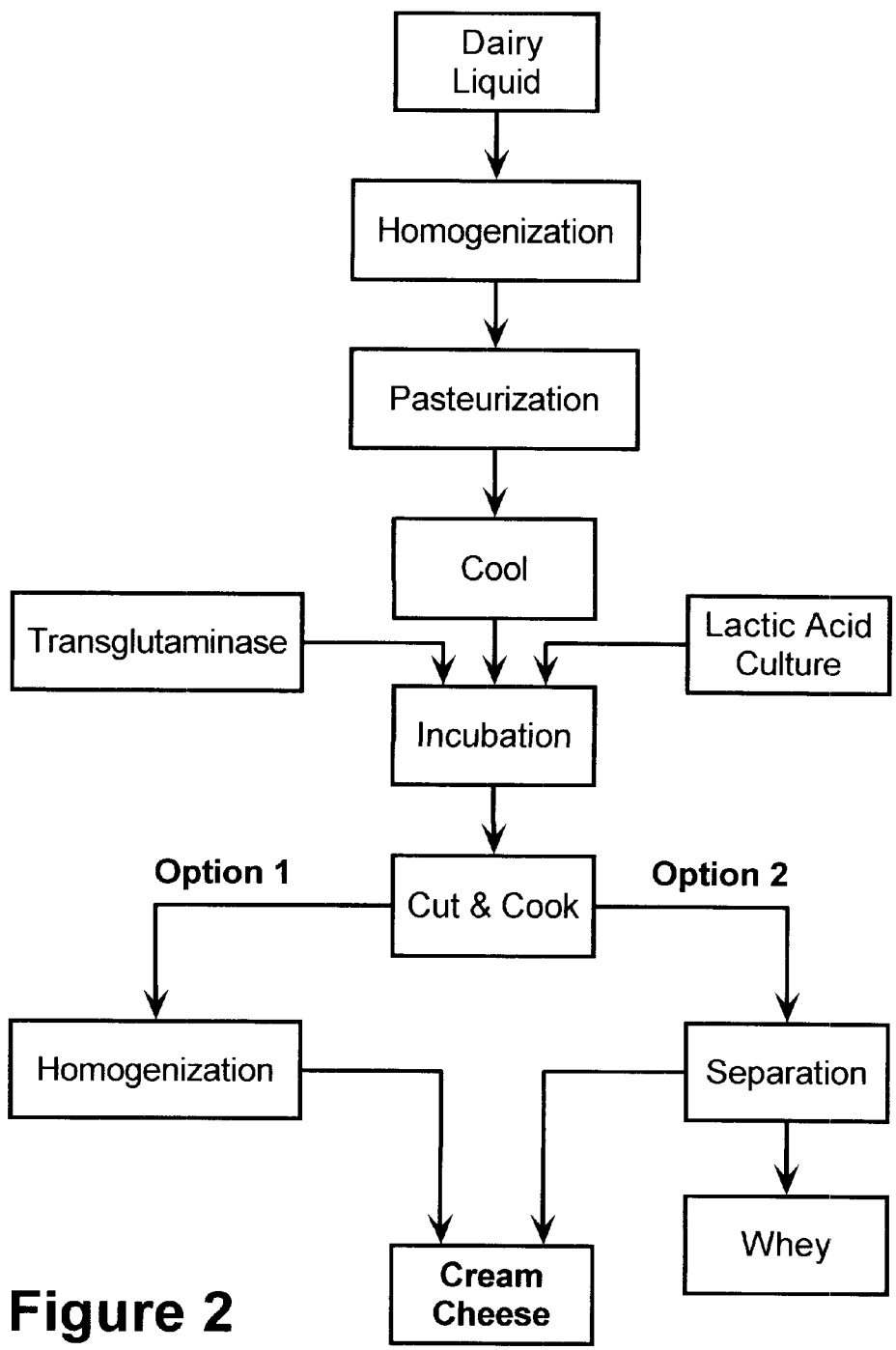
FIG. 2 is a more detailed flow diagram of illustrating the preparation of cream cheese using the process of this invention.

The present invention is especially adapted for, but not limited to, the production of cream cheese and cottage cheese. The dairy liquids used for a given process of the current invention are typically chosen based on the type of cheese product desired. For example, cream-added dairy liquid is used in the manufacture of cream cheese to balance and/or obtain target compositions in the final product which may be full-fat, fat-free, light, or reduced-fat cream cheese or Neufchatel. A detailed process flowchart illustrating the production of cream cheese using the present invention is shown in FIG. 2. As is known in the art, the cream-added dairy liquid for the production of cream cheese products normally has a butterfat content of from less than about 1 up to about 14 percent (and in certain cases up to as much as 20 percent), so that after processing, the finished cream cheese product will have a butterfat content of from less than about 1 up to about 35 percent (and in certain procedures, such as wheyless procedures, up to as much as 38 percent).

Figure 3:
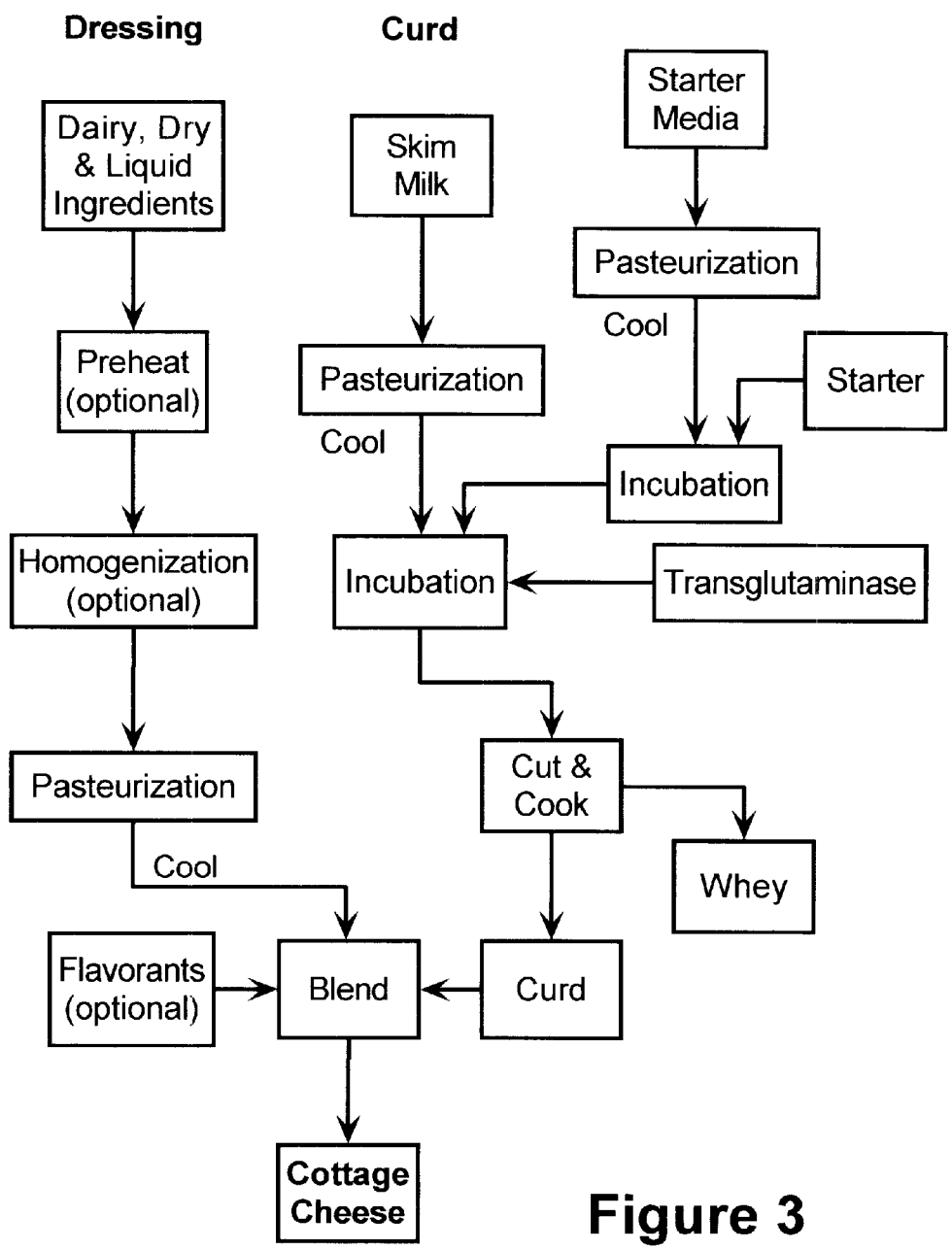
FIG. 3 is a more detailed flow diagram of illustrating the preparation of cottage cheese using the process of this invention.

A detailed process flowchart illustrating the production of cottage cheese using the present invention is shown in FIG. 3. For the production of such a cottage cheese product, dairy liquids are usually chosen from skim milk, skim milk concentrate, and reconstituted non-fat dry milk.

For certain embodiments, such as, but not limited to, the production of cream cheese, the dairy liquid is typically homogenized. Homogenization methods are well known in the food sciences. Any homogenization method that can be used to homogenize dairy liquids before processing into a cheese product can be used with the current invention. For example, but not intended to be limiting, cream-added milk for the production of cream cheese can be homogenized in a two-stage homogenizer. Preferably, the first stage is operated at a pressure of about 1000 to about 10000 psi and the second stage at about 100 to about 1000 psi.

A "pasteurized dairy liquid" is a dairy liquid that has been subjected to pasteurization. The process of pasteurization is well known in the art of food sciences. Pasteurization may or may not be applied in the current invention. Any method for pasteurization can be used for the current invention. For example, but not intended to be limiting, pasteurization of dairy liquids may be carried out by heating the dairy liquid under conventional pasteurization conditions such as, for example, but not limited to, about 72 to about 80° C. for at least about 15 seconds.

Dairy liquids used in the current invention may incorporate other ingredients. For example, calcium may be added for calcium fortification. Suitable calcium sources include, for example, calcium chloride, calcium sulfate, calcium phosphate, calcium citrate, calcium carbonate, calcium gluconate, and the like. Such other ingredients that can be used in the process of manufacturing cheese should not, of course, interfere with transglutaminase activity so as to completely inhibit the ability of this enzyme to crosslink proteins found in dairy liquids.

Figure 4:
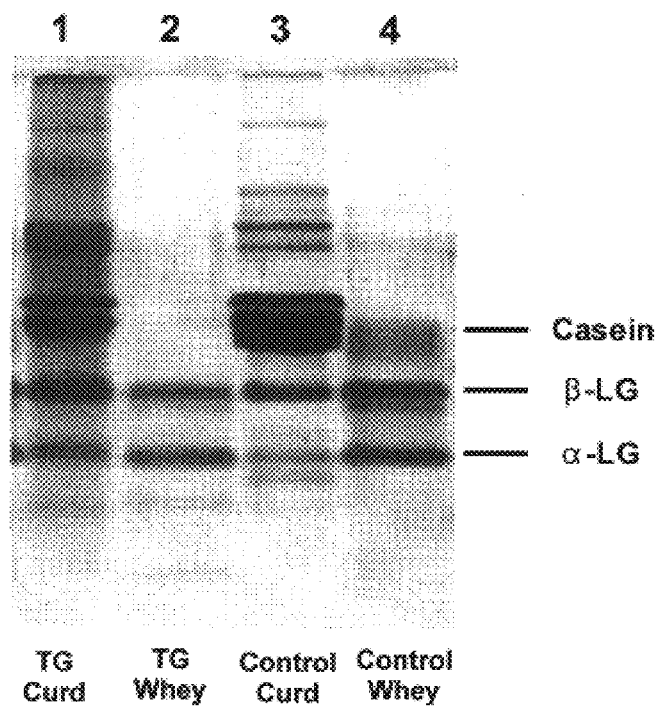
FIG. 4 is a Coomassie-stained 16.5% Tricine-SDS PAGE gel of samples obtained during the product of a cottage cheese curd according to Example 3. Lane 1: curd recovered from the transglutaminase-treated milk sample; Lane 2: whey recovered from the transglutaminase-treated milk sample; Lane 3: curd recovered from the control sample; Lane 4: whey recovered from the control sample. Whey and curd samples were loaded with the same quantity of whey and curd, respectively.

In the process of the current invention, the dairy liquids are curded and crosslinked by the addition of an acidifying agent and transglutaminase. For the current invention, crosslinking occurs during the curding process of the cheese-manufacturing process. Typically, the crosslinking agent is added to the dairy liquid at the same time the acidifying agent is added or shortly thereafter. Preferably, the crosslinking agent is added within 1 hour of addition of the acidifying agent, more preferably within 10 minutes of addition of the acidifying agent, and most preferably, immediately after addition of the acidifying agent. Delayed addition of transglutaminase results in a lesser degree of crosslinking with the same enzyme dosage. The degree of crosslinking should be sufficient to provide the desired textural and protein retention characteristics. In the current invention, crosslinking at least a portion of the dairy proteins can be detected using an SDS-PAGE gel and detecting a diminution of main protein bands compared to control, untreated cultures or by detecting a band of aggregates/polymers in SDS-PAGE gels. Preferably, the protein aggregates/polymers remain small enough to enter the stacking gel of the gel. FIG. 4 provides a typical gel with curd and whey from the process of this invention as well as curd and whey from a similar process run without transglutaminase.

Curding and crosslinking are carried out simultaneously and proceed at different rates of reaction during the entire process of curd formation as system conditions change (e.g., changes in pH, lactose content, protein substrates, and the like as the reactions proceed). When lactic acid-producing cultures are used as the acidifying agent, curding and crosslinking are carried out until the pH of the dairy liquid is reduced to a pH of about 4.2 to about 5.2, preferably about 4.4 to about 4.8, most preferably about 4.5 to about 4.7. Typically, the curding and crosslinking are carried out for between 1 and about 24 hours at temperatures of between about 18 and 55° C.

Typically, where the resulting cheese is cottage cheese, the crosslinking and curding time is from about 1 hour to about 14 hours and the crosslinking and curding conditions include temperature of about 22 to about 36° C., preferably from about 3 hours to about 6 hours at a temperature of about 30 to about 34° C.

Typically, where the resulting cheese is cream cheese, the crosslinking and curding time is from about 12 hours to about 24 hours and the crosslinking and curding conditions include temperature of about 20 to about 30° C., preferably from about 15 hours to about 19 hours at a temperature of about 22 to about 28° C. In one embodiment, the crosslinking and curding is carried out for about 17 hours at a temperature of about 25° C.

Typically, the curding and crosslinking is done without disturbing the dairy liquid being processed (i.e., without significant agitation). The acidifying agent may be either a food grade acid or a lactic acid-producing culture, both of which are well known in the art. Food grade acids, include, but are not limited to, citric acid, lactic acid, glucono delta lactone, phosphoric acid, acetic acid or vinegar, and the like.

Preferably, for the current invention, the acidifying agent is a lactic acid-producing culture. Such cultures are well known in the art of food science. Any lactic acid-producing bacteria used in conventional cheesemaking can be used in the process of the current invention. Not to be limited by theory, as is known in the art, lactic acid-producing microbes are used in cheese manufacturing to ferment lactose present in the dairy liquid and to cause further decomposition of the clotted casein into smaller peptides and free amino acids as a result of the culture's production of proteases and peptidases. The lactic acid-producing culture may be added in amounts which are conventional for the present purpose (i.e., typically about 10,000 to 10,000,000 bacteria/g of dairy liquid). The cultures may be added as freeze-dried, frozen, or liquid cultures.

As is well known in the art, the lactic acid-producing culture can be added as a starter culture. The starter culture is typically established by inoculating a lactic acid-producing bacteria into a relatively small quantity of dairy liquid compared to the quantity to be used in the cheese production process. The culture is incubated at a temperature that supports multiplication of the bacteria before being used to inoculate the full volume of dairy liquid for the batch of cheese production.

For the current invention, crosslinking of the dairy liquid occurs while the lactic acid-producing culture is acidifying the dairy liquids. By "crosslinking the dairy liquid" is meant crosslinking proteins present in the dairy liquid. Crosslinking of proteins during the process of the current invention is catalyzed by transglutaminase. Transglutaminases are enzymes which catalyze the transfer of the γ-carboxamide group of a glutaminyl residue in a protein or peptide to the ε-amino of a lysyl residue of the same or a different protein or peptide, thereby forming a γ-carboxyl-ε-amino crosslink.

Transglutaminases have a broad occurrence in living systems, and may be obtained, for example, from microorganisms such as those belonging to the genus Streptoverticillium, from *Bacillus subtilis*, from various Actinomycetes and Myxomycetes, from fish species and other marine sources, from plant sources, and from animal sources, especially mammals. For example, mammals provide the blood clotting protein activated Factor XIII; liver transglutaminase can be obtained, for example, from pigs. In general, transglutaminases from animal sources require calcium ions for activity. Recombinant forms of transglutaminase enzymes may be obtained by genetic engineering methods as heterologous proteins produced in bacterial, yeast, and insect or mammalian cell culture systems. The principal requirement of any transglutaminase employed in the instant invention is that it has the activity referred to above. Any enzyme having transglutaminase activity may be employed in the methods of the present invention. In a preferred embodiment, the transglutaminase is obtained from the genus Streptoverticillium.

Transglutaminase activity may be determined using known procedures. One such colorimetric procedure uses benzyloxycarbonyl-L-glutaminyl-glycine and hydroxylamine to form a γ-carboxyl-hydroxamic acid if transglutaminase is present. An iron complex of the hydroxamic acid can be formed in the presence of ferric chloride and trichloroacetic acid. Using the absorbance at 525 nm with appropriate standards, the activity of enzyme present may be determined (see, e.g., U.S. Pat. No. 5,681,598 and *J. Biol. Chem.* 240:2951 (1965)).

In certain embodiments, transglutaminase is used in step (ii) at concentrations of less than 10 units per gram of dairy liquid, preferably less than 5 units per gram, more preferably less than 1 unit per gram of dairy liquid. In certain embodiments, transglutaminase is used at a concentration of about 0.4 to about 0.8 units per gram of dairy liquid.

After crosslinking and curding, the curd is disturbed and cooked. Typically, the curd is disturbed by cutting or stirring. The processes of cutting or stirring and cooking curd are well known in the art. Examples of cooking conditions are described in the accompanying Examples section. For example, but not intended to be limiting, where the cheese is cream cheese, the cooking can be performed by heating the temperature of the curd and whey to about 80° C. for about 30 minutes. In another embodiment where the dairy liquid is skim milk, the cooking in step (iv) can be performed by increasing the temperature of the curd and whey from about 30 to about 60° C. over a period of about 60 minutes.

After being cut and cooked, the curd is separated from the whey and the curd is collected (see, e.g., Option 2 in FIG. 2). Methods are well known in the art for separating curd from whey and collecting curd. These methods may vary depending on the type of cheese produced. For example, but not intended to be limiting, centrifugation by a separator (e.g., a Model #KSA6-01-076 separator, Westfalia Separator, Inc., Northvale, N.J.) can be used to separate curd from whey during cream cheese production. Alternatively, the curd and whey can be homogenized without separation (see, e.g., Option 1 in FIG. 2).

Typically, a conventional milk clotting/renneting enzyme is not present during the curding and crosslinking step in the processes of the current invention. In certain embodiments, a conventional milk clotting/renneting enzyme is not present during any step of the process. A "conventional milk clotting/renneting enzyme" is a rennet or a non-rennet protease that has coagulating activity.

Rennet is a generic term used in the field of dairy science and in the field of cheese making, to designate an activity obtained from the lining of the stomachs of immature mammals that consume maternal milk. The natural function of rennet is to initiate the digestion of the milk in order to provide the nutrition contained in the milk protein to the young mammal. In cheese making, rennet is used to clot the dairy liquids, thereby forming cheese curd and whey. The term "renneting" relates to the process of treating a dairy liquid with a rennet to provide a cheese curd and whey. Synonyms for "renneting" include "curding," "clotting," and "setting." As used in contemporary dairy science, "rennet" connotes the enzyme earlier called "rennin" and now termed "chymosin." Chymosin is a member of the family of proteases known as aspartyl endopeptidases.

The activity of chymosin on dairy liquids includes at least the proteolytic cleavage of the peptide bond between the phenylalanyl residue that occurs at about position numbered 105 and the methionine that occurs at about position numbered 106 in κ-casein to release a soluble macropeptide and induce the coagulation of the remainder of the molecule, termed para-κ-casein, with all the components of the casein micelles. Common natural sources of chymosin include, but are not limited to, the stomachs of calves, buffalo, other ruminants, kid goats, lambs, piglets, and the like. Furthermore, various natural chymosins and genetically engineered chymosin mutant proteins are available as the recombinant protein products, obtained as a result of introducing genes encoding these proteins as heterologous genes in order to make the gene products in suitable host organisms. Chymosin is the activated form produced when the proenzyme prochymosin is activated. Prochymosin likewise may be a recombinant product, and may be a genetically engineered mutant protein which upon activation provides renneting activity. As used herein, all such chymosins having renneting activity, and prochymosins activatable to such chymosins, are included in the term "rennet."

Many other non-rennet enzymes have coagulating activity. Nonlimiting examples include other aspartyl proteases such as various pepsins, and a large number of proteases from nonmammalian sources, including plants, microorganisms, and marine fishes. As used herein, a "non-rennet protease" relates to any such protease having milk-clotting activity that is not a rennet as defined herein. Furthermore, various natural non-rennet proteases, as well as genetically engineered mutant proteins derived from such natural proteases and having the corresponding protease activity, are available as recombinant protein products, obtained upon introducing genes encoding these proteins as heterologous genes into suitable host organisms to produce the protein products. As used herein, all such recombinant non-rennet proteases having milk-clotting activity are included in the term "non-rennet protease."

Among the non-rennet proteases that may be used in the process of dairy liquid curding are the bacterial protease obtained from *Bacillus licheniformis* and designated SP 446 (Novo Nordisk), the bacterial protease from *Bacillus thermoproteolyticus*, the microbial protease Coralase PN-L produced by *Aspergillus sojae* (Rohm GmbH, Germany), a plant protease such as papain, animal proteases such as a protease from the intestines of fishes.

The cooked curd produced by the process of the current invention can be combined with other ingredients to obtain final cheese products. These other ingredients include any ingredients typically used in cheese manufacturing. For example, dressings can be added to the curd for the production of creamed cottage cheese (see, e.g., FIG. 3).

The processes of the current invention may include an additional homogenization step after the curd is collected. Preferably, a single- or two-stage homogenizer can be used. Preferably, the first stage is operated at a pressure of about 1000 to about 10000 psi and the optional second stage at about 100 to about 1000 psi.

In another aspect, the current invention relates to cheese products, especially cream cheese and cottage cheese products, produced by a process as described above, including any of the embodiments described above. The cheese products of the current invention have a number of advantages. For example, the processes of the current invention significantly increase the yield of cheese produced while reducing processing time. The cheese products are less fragile and have reduced syneresis. Additionally, the cheese products have greater viscosity and firm texture. Not to be limited by theory, it is believed that these advantages are the result, at least in part, of smaller, more concentrated protein particles observed in cheese products produced by processes of the current invention (see, e.g., FIG. 6).

The following examples describe and illustrate the processes and products of the invention. These examples are intended to be merely illustrative of the present invention, and not limiting thereof in either scope or spirit. Unless indicated otherwise, all percentages and ratios are by weight. Those skilled in the art will readily understand that variations of the materials, conditions, and processes described in these examples can be used.

EXAMPLE 1

Effect of Transglutaminase Dosage on the Incorporation of Whey Protein into Cottage Cheese An analysis was performed of the effect of transglutaminase on the incorporation of whey protein into cottage cheese. The process used for making cottage cheese consisted of the following steps:

(1) Skim milk was pasteurized at about 72° C. for 15 seconds.

(2) A starter culture was prepared by inoculating the pasteurized milk with a lactic acid-producing culture at 22° C. and incubating overnight.

(3) The starter culture (6.0 kg) was mixed with 94.0 kg of pasteurized skim milk at 32° C.

(4) During the process of fermentation, transglutaminase was added to the samples at the quantities shown in Table 1.

(5) The samples were incubated at 32° C. for about 5 hours to lower pH to about 4.70.

(6) Curd was cut and incubated undisturbed for 30 minutes.

(7) Temperature was increased from 30° C. to 60° C. over a period of about 60 minutes.

(8) The curd was drained using cheesecloth.

Protein concentrations were determined using the Lowry assay (Lowry, O. H., Rosebrough, N. G., Farr, A. L., and Randall, R. J., "Protein Measurement with Folin phenol reagent," *J. Biol. Chem.* 193:265 (1951)). Transglutaminase activity was determined as described in *J. Biol. Chem.* 240:2951 (1965). One unit of transglutaminase activity is defined as the amount of enzyme that catalyzes the formation of 1 micromole of hydroxymate per minute under the assay conditions.

Figure 5:
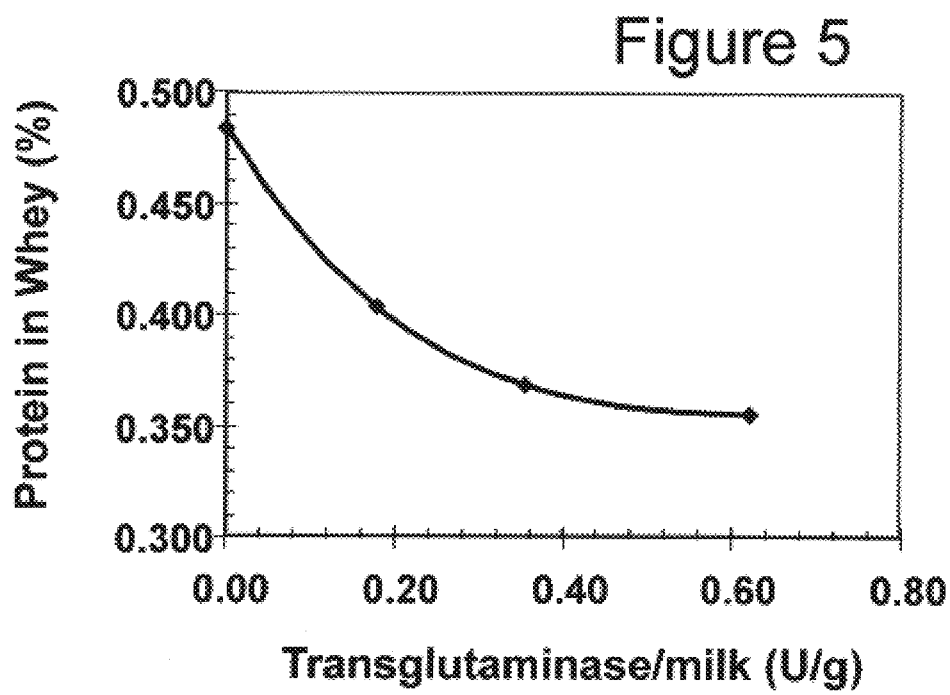
FIG. 5 is a graph of the percent concentration of proteins in whey as a function of the final concentration of transglutaminase in milk used in the process according to Example 1.

Experimental results are summarized in Table 1. The concentration of proteins in the recovered whey decreased with increasing dosage of transglutaminase. Compared to the control sample which had no added transglutaminase, up to 26 percent of whey protein was incorporated into cottage cheese curd. FIG. 5 shows the relationship between the activity of transglutaminase added to milk and the concentration of proteins in the whey. Of course, decreasing whey protein in the whey corresponds to increasing whey protein in the curd. In addition to the incorporation of whey proteins into curd that caused a significant increase in the yield of curd, the firmness of cottage cheese curd was also significantly increased by the reaction of transglutaminase cross-linkage.

TABLE 1

Effect of Transglutaminase (TG) Dosage on the Incorporation of Whey Protein into Cottage Cheese

| Sample | | Proteins in Whey | Proteins in Whey |
|---|---|---|---|
| No. | Milk (g) | TG (g) | ($A_{660}$ nm)* | (%) |
| 1 | 225 | 0 | 0.3074 | 0.484 |
| 2 | 225 | 0.40 | 0.2564 | 0.404 |
| 3 | 225 | 0.80 | 0.2339 | 0.368 |
| 4 | 225 | 1.40 | 0.2257 | 0.355 |

*Whey recovered was diluted 10X for the assay. Data are mean values of triplicate measurements.

EXAMPLE 2

Denatured Transglutaminase Has No Affect on Whey Protein Incorporation

An analysis was performed to determine whether the effects of transglutaminase on the incorporation of whey proteins into cottage cheese required the transglutaminase enzyme to be active. The process for making cottage cheese was carried out as described in Example 1 except that either denatured or active transglutaminase were added to the culture as shown in Table 2. Additionally, the formed curd was cut after about 4 hours incubation at 32° C. instead of about 5 hours incubation as in Example 1. Protein concentration and transglutaminase activity was measured as described in Example 1.

Results of the experiment are summarized in Table 2. This experiment further confirms that the decreased protein concentration in recovered whey is caused by the cross-linking of transglutaminase. Heat denatured transglutaminase had no effect on the incorporation of whey protein into cheese curd. The concentration of proteins in whey recovered from the sample with the addition of heat denatured transglutaminase was the same as that of control samples, indicating that the components in the inactivated enzyme sample had no effect on whey protein incorporation. On the other hand, up to 23 percent of whey protein was incorporated into cottage cheese curd with the addition of 0.60 g of active transglutaminase (100 units/g).

TABLE 2

Experimental Design and Results

| | Sample | | Proteins in Whey | Proteins in Whey |
|---|---|---|---|---|
| No. | Milk (g) | TG (g) | ($A_{660}$ nm)* | (%) |
| 1 | 400 | 0 | 0.7367 | 0.464 |
| 2 | 400 | 0.60 (denatured) | 0.7361 | 0.464 |
| 3 | 400 | 0.60 | 0.5577 | 0.351 |
| 4 | 400 | 0.60 | 0.5678 | 0.358 |
| 5 | 400 | 0.60 | 0.5776 | 0.364 |

*Whey recovered was diluted 5x for the assay. Data are mean values of triplicate measurements.

EXAMPLE 3

Pilot Plant Testing of the Process for Incorporating Whey Protein into Cottage Cheese An analysis was performed of the ability of the process of the current invention to increase the amount of protein incorporated in cottage cheese when carried out in a larger batch size. The process used was a modified version of the process described in Example 1. The pilot plant process used for making cottage cheese consisted of the following steps:

(1) Skim milk was pasteurized at about 72° C. for 15 seconds.
(2) A starter culture was prepared by inoculating the pasteurized milk with a lactic acid-producing culture at 22° C. and incubating overnight.
(3) The starter culture (12.7 kg) was mixed with 215 kg of pasteurized skim milk at 32° C.
(4) During the process of fermentation, transglutaminase (0.68 kg enzyme powder dissolved in 2.8 kg water) was added to the sample and the sample was mixed.
(5) The samples were incubated at 32° C. for about 4 hours to lower pH to about 4.70.
(6) Curd was cut and incubated undisturbed for 30 minutes.
(7) Temperature was increased from 30° C. to 55° C. over a period of about 120 minutes.
(8) The curd was drained then washed with water twice.
(9) The washed curd was drained, weighed, and mixed with dressing (prepared as shown diagrammatically in FIG. 3) to make the final cottage cheese product.

Control samples were processed as above except that no transglutaminase was added. The activity of the transglutaminase used in this experiment was 100 Unit/g enzyme powder. Moisture content was determined using a vacuum oven test. For this test, the weight of curd was determined before and after drying the curd in a vacuum oven.

Protein concentrations and transglutaminase activity were determined as described in Example 1. Whey samples were filtered to remove fine particles and diluted 10×before determining their protein concentration by the Lowry assay. Protein composition of curd and whey fractions were analyzed by Coomassie blue R-250 staining of proteins separated by electrophoresis on 16.5% SDS polyacrylamide gels, according to the method of Laemmli, U.K., *Nature*, 227:680 (1970). A typical gel is shown in FIG. 4 for both inventive curd and whey and for control curd and whey.

Figure 6:
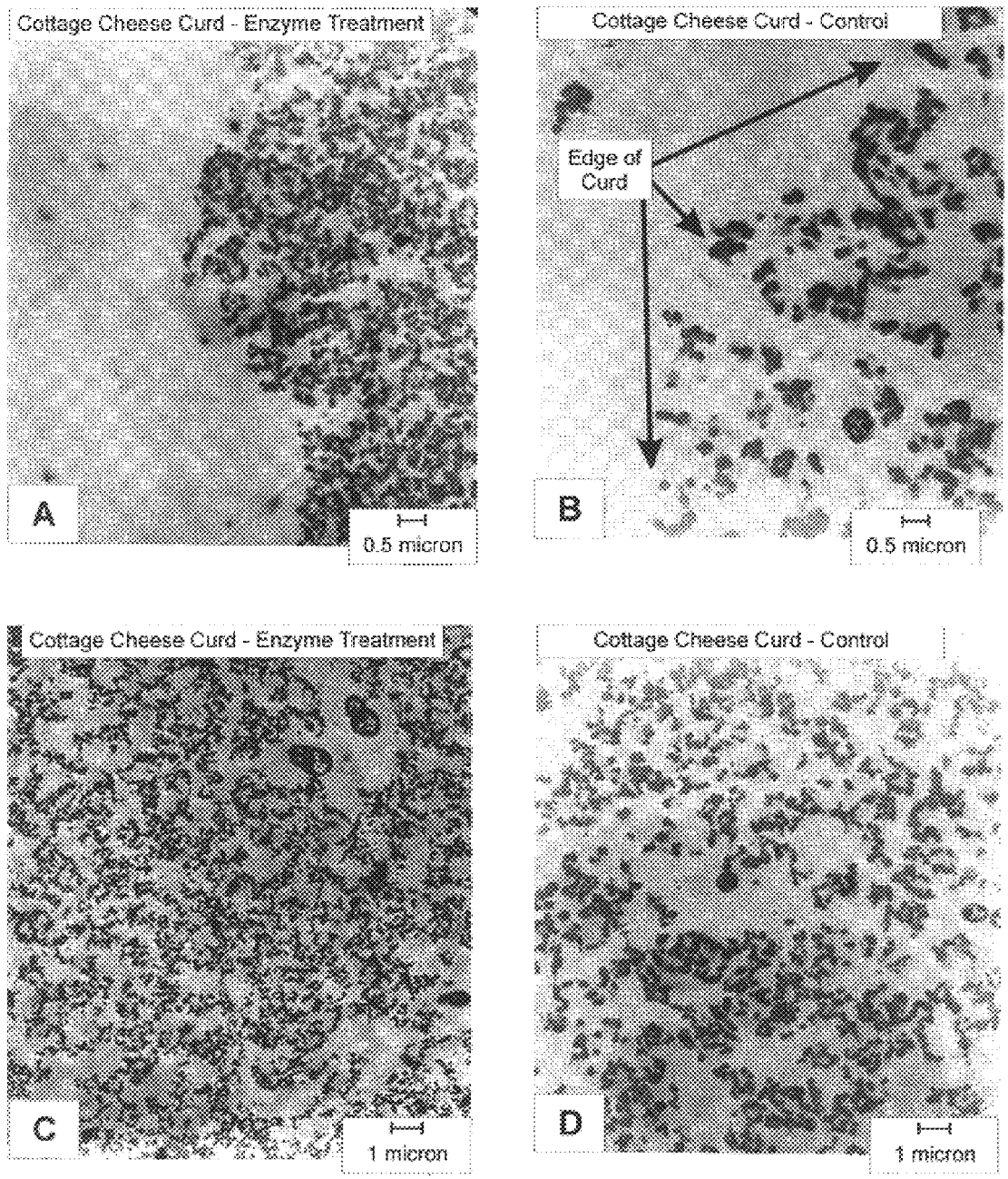
FIG. 6 contains electron micrographs of cottage cheese curd produced by the method of this invention according to Example 3. Panels A and B illustrate the cottage cheese edge produced with transglutaminase (A) and without transglutaminase (B). Panels C and D illustrate the cottage cheese curd body produced with transglutaminase (C) and without transglutaminase (D).

Transmission electron microscopic analysis was performed using standard procedures known in the art, as described in HAYAT's *Principles and Techniques of Electron Microscopy,* Litton Educational Publishing, Inc. The samples were counterstained with osmium tetroxide ($OSO_4$) and analyzed using a ZEISS model EM10 transmission electron microscope. FIG. 6 provides typical electron micrographs of cottage cheese curd produced.

Results of the experiment are summarized in Table 3. Compared to control samples (i.e., no added transglutaminase), 23 percent of whey protein was incorporated into the cottage cheese curd in samples containing added transglutaminase. The incorporation of whey proteins into curd caused a significant increase in the yield of curd (39.6 kg vs. 31.7 kg). Total curd solids recovered from transglutaminase-treated milk was 26 percent greater than that from control sample. The application of transglutaminase to cottage cheese production, therefore, yields significant productivity savings.

TABLE 3

Differences Between Transglutaminase-treated Sample and Control

| | Transglutaminase Treated | Control |
|---|---|---|
| Proteins in Whey ($A_{660}$ nm)* | 0.212 | 0.276 |
| Curd Obtained (kg) | 39.6 | 31.7 |
| Moisture in Curd (%) | 78.1 | 78.4 |
| Total Solids in Curd (kg) | 8.67 | 6.85 |

*Protein content in the whey samples was 3.87% for the control sample and 2.97% for the transglutaminase-treated sample, according to this assay. Data are mean values of triplicate measurements.

In addition to the increase in curd yield, the texture of cottage cheese curd was significantly improved (i.e., increase in firmness) by transglutaminase cross-linking. Analysis of the microstructure of curd samples indicated that transglutaminase-treated curd contained smaller protein particles with less empty space between the particles (see FIG. 6). This reduced empty space (both at the edges and the body of the curd) likely contributes to the reduced rate of syneresis and the unique texture of the cottage cheese of this invention. Thus, it appears that transglutaminase cross-linking significantly effects both the microstructure of the curd and the incorporation of whey protein in the curd. It also appears that the less-fragile curd resulted in fewer fine particles of curd being lost in the whey. A cooked egg-white-like texture was produced with the cross-linking using transglutaminase. The texture is very unique for curd. The significantly firmer texture of curd formed from transglutaminase-cross-linking reduces the need for gentle handling of curd during the initial stages of cooking, resulting in a more robust process.

FIG. 4 shows the protein profile of curd and whey recovered from the pilot plant process and a control process without added transglutaminase. Compared to whey recovered from control samples, whey recovered from transglutaminase-treated milk contained fewer proteins, especially caseins. Based on the small amount of proteins remaining in the whey of transglutaminase-treated samples (FIG. 4, lane 2), it may be difficult to incorporate further β-lactoglobulin and/or α-lactobumin into curd. Transglutaminase treatment produced protein polymers with a wide range of molecular weights (FIG. 4, lane 1). These polymers likely contribute to the unique texture of the cottage cheese curd obtained. The texture of cheese curd, therefore, can be adjusted by controlling cross-linking conditions.

EXAMPLE 4

Effect of Transglutaminase Dosage on the Incorporation of Whey Protein into Cream Cheese An analysis was performed of the effect of transglutaminase on the incorporation of whey protein into cream cheese. The process used for making cream cheese consisted of the following steps:

(1) Cream-added milk was homogenized in two stages at a pressure of 1600 psi in the first stage and 500 psi in the second stage and pasteurized at about 72° C. for 15 seconds. The milk/cream ratio was 0.743/0.257. The full fat milk contained 12.0% solids, 88.0% moisture, 3.6% fat, and 3.2% protein. The cream contained 45.5% solids, 54.5% moisture, 41.0% fat, and 2.0% protein.

(2) The pasteurized cream-added milk was inoculated with 0.75 percent volume of a bulk culture of a lactic acid-producing culture at 25° C.

(3) During the process of fermentation, transglutaminase was added to the samples at the quantities shown in Table 4.

(4) The samples were incubated without disturbance at about 25° C. for about 17 hours to lower pH to about 4.50.

(5) The coagulum was stirred and the sample was heated to 80° C. and held for 30 minutes.

(6) The curd was separated from the whey by centrifugation at 1500 rpm for 10 minutes.

Protein concentrations and transglutaminase activity was determined as described in Example 1. Recovered whey was diluted 10× for protein concentration determinations. Control samples were prepared using a process identical to that described above except that no transglutaminase was added or the added transglutaminase (20 percent w/v) was heat denatured by heating to 85° C. for 10 minutes before addition to the pasteurized milk. The percent of whey protein incorporated into transglutaminase-added samples was determined by subtracting the $A_{660}$ of whey samples from processes where active transglutaminase was used from the $A_{660}$ of whey samples from processes where heat-treated transglutaminase was used and dividing the remainder by 0.373.

Results of the experiment are summarized in Table 4. The concentration of proteins in the recovered whey decreased with increasing dosage of transglutaminase. Compared to control samples without added transglutaminase, up to 19 percent of whey protein was incorporated into cream cheese curd. Heat denatured transglutaminase had no effect on the incorporation of whey protein into cheese curd. The concentration of proteins in whey recovered from the sample with the addition of heat denatured transglutaminase was the same as that of control samples without added transglutaminase, indicating that the components in the inactivated enzyme sample had no effect on whey protein incorporation. A number of benefits were found with the addition of transglutaminase during the cream cheese manufacturing process, in addition to the increased utilization of starting milk protein. For example, the incorporation of whey proteins into curd caused an increase in the yield of curd. In addition, the firmness and viscosity of cream cheese curd was significantly increased by the transglutaminase cross-linkage.

TABLE 4

Effect of Transglutaminase (TG) Dosage on the Incorporation of Whey Protein into Cream Cheese

| No. | Sample Milk (g) | TG (g) | Proteins in Whey ($A_{660}$ nm)* | Whey Protein Incorporated (%) |
|---|---|---|---|---|
| 1 | 500 | 0 | 0.373 | 0.0 |
| 2 | 500 | 0.40 (heated) | 0.375 | 0.0 |
| 3 | 500 | 0.20 | 0.347 | 7.0 |
| 4 | 500 | 0.40 | 0.322 | 14.2 |
| 5 | 500 | 0.80 | 0.315 | 18.2 |
| 6 | 500 | 1.50 | 0.331 | 19.3 |
| 7 | 500 | 1.50 (heated) | 0.403 | 0.0 |

*Whey recovered was diluted 10× for the assay. Data are mean values of triplicate measurements.

EXAMPLE 5

Pilot Plant Testing of the Process for Incorporating Protein into Cream Cheese

An analysis was performed of the of the process of the current invention to increase the amount of protien incorporated in cream cheese, when carried out in a larger batch size. The process used was a modified version of the process described in Example 4. The pilot plant process used for making cream cheese consisted of the following steps:

(1) Cream-added milk (1362 kg total, 997 kg milk mixed with 365 kg cream) was homogenized in two stages, at a pressure of 1600 psi in the first stage and 500 psi in the second stage, and pasteurized at or above 72° C. for 15 seconds.

(2) The pasteurized cream-added milk was inoculated with 0.75 percent volume of a bulk culture of a lactic acid-producing culture at 25° C.

(3) During the process of fermentation, 2.0 kg of transglutaminase dissolved in 10 kg of water was added to the sample.

(4) The samples were incubated without disturbance at about 25° C. for 17 hours to lower pH to about 4.50.

(5) The mixture was heated to about 82° C. by pumping it to a plate exchanger.

(6) The mixture was then pumped to a separator (Model #KSA6-01-076, Westfalia Separator, Inc., Northvale, N.J.) and separated at 82° C.

(7) A slurry of whey, salt, and/or gum mixture was added to the separated curd and moisture was adjusted to 60 percent.

(8) The sample was homogenized at 0, 1500, 3500, and 5000 psi.

(9) The sample was hot filled and stored at 4° C. after 15 minutes incubation after filling.

Protein concentrations in the cheese samples were determined using the Kjeldahl method (Bradstreet, R. B., "The Kjeldahl Method for Organic Nitrogen," Academic Press, Inc., New York, N.Y. (1965); Official Methods of Analysis, 14th Ed., AOAC, Arlington, Va., Methods No. 2.057, 24.038–24.040 (1985)) using a KJELTEC AUTO 1030 Analyzer (Fisher Scientific, Itasca, Ill.).

Protein concentrations in the whey samples recovered were determined using the Lowry assay (Lowry, O. H., Rosebrough, N. G., Farr, A. L. and Randall, R. J., "Protein measurement with Folin phenol reagent," *J. Biol. Chem.* 193:265 (1951)). Transglutaminase activity was determined as described in Example 1.

Recovered whey was diluted 10×for protein concentration determinations. Control samples were prepared using a process identical to that described above except that no transglutaminase was added. The percent of whey protein incorporated into transglutaminase-added samples was determined by subtracting the $A_{660}$ of whey samples from processes where active transglutaminase was used from the $A_{660}$ of whey samples from processes where heat-treated transglutaminase was used and dividing the remainder by 0.274.

Moisture content was determined using a vacuum oven test. For this test, the weight of curd was determined before and after drying the curd in a vacuum oven.

Viscosity of the samples was measure at 4° C. using a Viscometer (Model HAAKE VT550, HAAKE Inc., Karlsruhe, Germany). Syneresis was measured after a 20-hour incubation at room temperature by determining the amount of moisture phase separated from the sample during the incubation period. For this measurement, the cheese sample in an 8 oz cup was cut in the middle and half of the sample removed completely to the bottom of the cup and its weight measured. After incubation, the moisture phase was removed and the net change in weight is the amount of moisture separated. The rate of syneresis=net change in weight divided by the original weight of the sample after cutting.

Fat concentration was determined by a standard method as described in the AOAC 16$^{th}$ Ed., 4$^{th}$ Revision, March 1998, method #33.7.17. Lactic acid concentration was determined by using an enzyme/spectrophotometric assay with a Boehringer Mannheim (Indianapolis, Ind.) test kit.

The process used for making cream cheese in the pilot plant for this experiment is shown in FIG. 9. Results of analysis of whey remaining after the manufacture of cream cheese using this pilot plant process are shown in Tables 5 and 6. Compared to control samples, which were manufactured without the addition of transglutaminase, 13.5 percent of whey protein was incorporated into cream cheese curd for the sample treated with transglutaminase (Table 5).

In addition to the incorporation of whey proteins into curd which caused an increase in the yield of curd, the texture/viscosity of the cream cheese curd was also significantly improved by the transglutaminase cross-linkage. Without post homogenization, the viscosity of transglutaminase-treated samples was 5.5 times greater than that of control samples. Cross-linking of proteins also minimized syneresis of the final product. The syneresis rate of the final product was decreased about 50 percent in the cream cheese curd prepared with the addition of transglutaminase. The increase in product viscosity and decrease in syneresis were further confirmed by repeated pilot plant experiments (data not presented). With the incorporation of whey protein as well as increased moisture in the sample of transglutaminase-treated milk, its fat content was lowered. In addition, the transglutaminase-treated sample contained less lactic acid, which should improve the flavor of the final product.

TABLE 5

Incorporation of Whey Protein into Curd by Transglutaminase (TG) Treatment

| Sample | Proteins in Whey (Average*; $A_{660}$ nm) | Whey Protein Incorporated (%)** |
|---|---|---|
| Transglutaminase Treated | 0.237 | 13.5 |
| Control Sample | 0.274 | 0.0 |

*Data are mean values of duplicated measurements.
**The rate of whey protein incorporation = ($A_{660}$ control − $A_{660}$ TG-treated)/0.274.

TABLE 6

Characteristics of Soft Cream Cheese Prototypes from Pilot Plant Experiment*

| | Homog. (Psi) | Moisture (%) | Viscosity (Pa) | Syneresis (%) | Fat (%) | Acidity (%) | Lac. Acid (%) | Proteins (%) |
|---|---|---|---|---|---|---|---|---|
| A | 0 | 61.1 | 3637 | 6.0 | 28.2 | 0.74 | 0.46 | 6.3 |
| | 5000 | 60.4 | 5912 | 5.5 | 28.8 | 0.71 | 0.42 | 6.3 |
| B | 0 | 58.9 | 656 | 11.1 | 31.0 | 0.79 | 0.49 | 5.9 |
| | 5000 | 58.4 | 5226 | 10.2 | 31.9 | 0.78 | 0.51 | 6.3 |

*Data are mean values of duplicate measurements.

Figure 7:
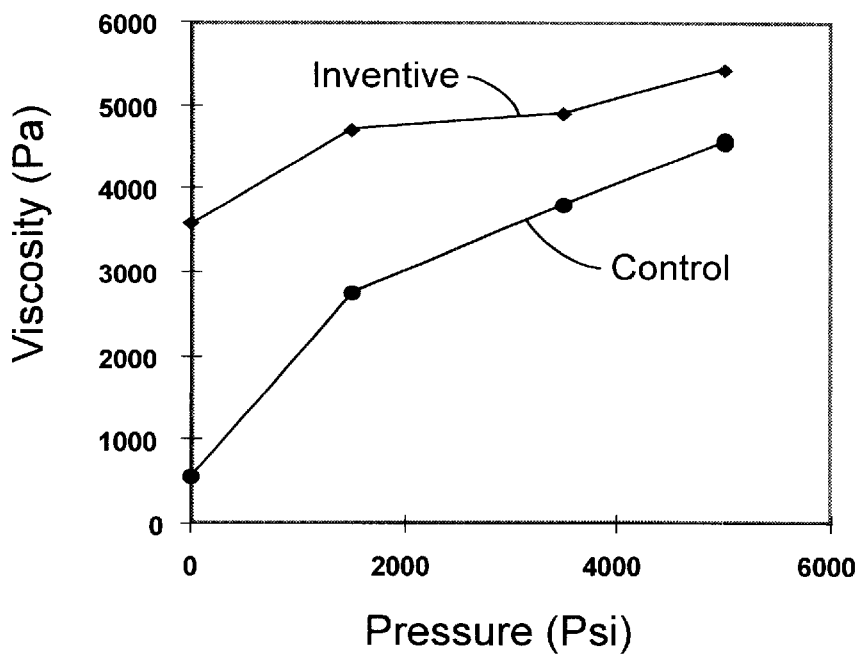
FIG. 7 is a graph of cream cheese viscosity (Pa) at various pressures of post-curd formation homogenization for samples produced by the process of this invention according to Example 5 using a transglutaminase addition step; a control sample without transglutaminase is also shown.

In addition to the effects of transglutaminase addition, the process of homogenization of the curd had significant effects on product texture and syneresis. As shown in FIG. 7, product viscosity increased with increasing homogenization pressure as expected. In addition, as mentioned above the viscosity of transglutaminase-added products was greater than that of control samples. In addition, the viscosity of transglutaminase-treated samples was almost linearly proportional to the pressure of homogenization, indicating that cross-linked protein conjugates are compatible with the fat globule and curd matrix.

Figure 8:
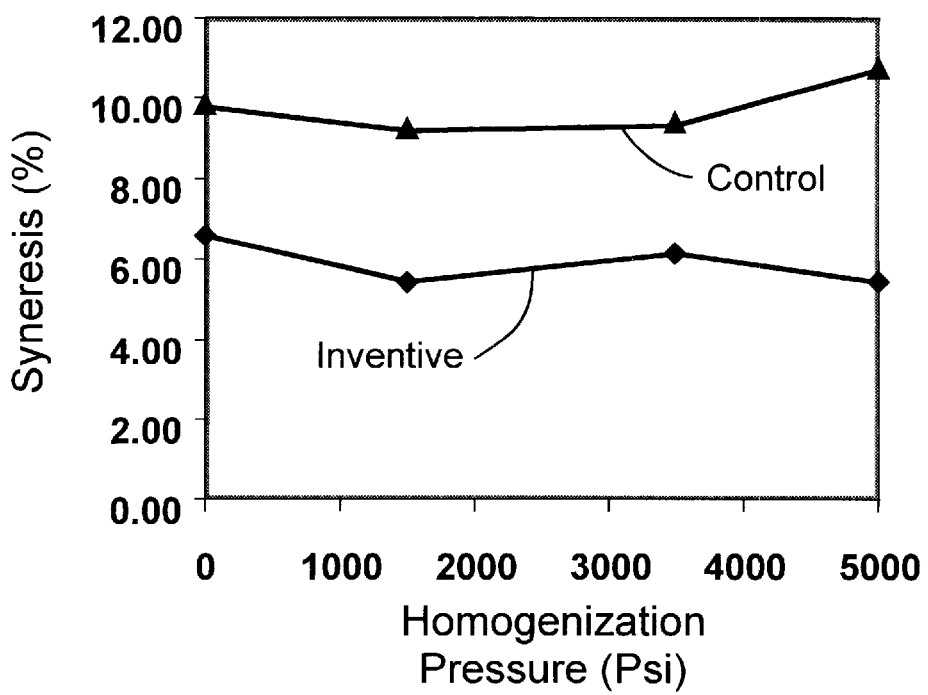
FIG. 8 is a graph of percent syneresis at various post curd formation homogenization pressures for cream cheese samples produced by the process of this invention according to Example 5 using a transglutaminase addition step; a control sample without transglutaminase is also shown.

The homogenization pressure applied to formed curd, however, had fewer effects on the rate of product syneresis. No significant change on the rate of syneresis was observed for control samples or transglutaminase-treated samples with increasing homogenization pressure (FIG. 8). As found in experiments described in previous Examples, transglutaminase-treated samples had reduced syneresis compared to control samples. The results reported in this Example support the conclusion that the process of the current invention produces firmer cream cheese products with minimized syneresis.

Throughout this application, various patents, publications, books, nucleic acid and amino acid sequences have been cited. The entireties of each of these patents, publications, books, and amino acid sequences are hereby incorporated by reference into this application.

What is claimed is:

1. A process for making a cheese product comprising:
   (i) providing a dairy liquid comprising dairy proteins;
   (ii) crosslinking and curding the dairy liquid by adding an acidifying agent and a transglutaminase to the dairy liquid for a crosslinking and curding time, and under crosslinking and curding conditions, sufficient to crosslink at least a portion of the dairy proteins and to form a curd and a liquid whey;

(iii) disturbing and heating the curd;

(iv) separating the curd from the liquid whey; and (v) collecting the curd.

2. The process of claim 1, wherein the acidifying agent can be added before or after the transglutaminase during step (ii).

3. The process of claim 2, wherein the process further comprises heating the crosslinked dairy liquid after step (ii) and before step (iii) at an inactivation temperature and an inactivation time sufficient to inactivate the transglutaminase.

4. The process of claim 3, wherein the acidifying agent is a culture containing a lactic acid-producing microbe and no conventional/milk clotting/renneting enzyme is used in the process.

5. The process of claim 3, wherein the acidifying agent is a food grade acid and no conventional/milk clotting/renneting enzyme is used in the process.

6. The process of claim 4, wherein the crosslinking and curding time is the time required to bring the pH of the dairy liquid to a pH of about 4.2 to about 5.2.

7. The process of claim 5, wherein the crosslinking and curding time is the time required to bring the pH of the dairy liquid to a pH of about 4.2 to about 5.2.

8. The process of claim 6, wherein the cheese is a cream cheese and the crosslinking and curding time is from about 1 hour to about 24 hours and the crosslinking and curding conditions comprise a temperature of about 18 to about 55° C.

9. The process of claim 6, wherein the cheese is a cottage cheese and the crosslinking and curding time is from about 1 hour to about 14 hours and the crosslinking and curding conditions comprise a temperature of about 15 to about 55° C.

10. The process of claim 6, wherein the cheese is a cream cheese and the dairy liquid comprises cream and a dairy ingredient selected from the group consisting of milk, reconstituted dry milk, concentrated milk, whey, whey protein concentrate, and milk protein concentrate.

11. The process of claim 10, wherein in step (iii) the heating is performed by bringing the temperature of the curd and whey to about 55 to 80° C. for about 1 to 60 minutes.

12. The process of claim 6, wherein the cheese is a cottage cheese and the dairy liquid is selected from the group consisting of milk, concentrated skim milk, reconstituted nonfat dry milk, whey protein, and milk protein concentrate.

13. The process of claim 12, wherein in step (iii) the heating is performed by increasing the temperature of the curd and whey from about 30 to about 60° C. over a period of about 15 to about 250 minutes.

14. The process of claim 6, wherein the transglutaminase is selected from the group of transglutaminases isolated from a bacterial source, a fungus, a mold, a fish, and a mammal.

* * * * *